United States Patent [19]
Steer et al.

[11] Patent Number: 5,495,858
[45] Date of Patent: Mar. 5, 1996

[54] MALE INCONTINENCE DEVICE

[75] Inventors: Peter L. Steer, East Grinstead; Graham D. Bannister, Lindfield; Howard Barrett, Dorking, all of United Kingdom

[73] Assignee: E. R. Squibb & Sons, Inc., Princeton, N.J.

[21] Appl. No.: 329,384

[22] Filed: Oct. 26, 1994

[30] Foreign Application Priority Data

Oct. 28, 1993 [GB] United Kingdom ............... 9322234
Sep. 5, 1994 [GB] United Kingdom ............... 9417824

[51] Int. Cl.⁶ .................................................. A61F 5/48
[52] U.S. Cl. ................................. 128/885; 128/DIG. 25
[58] Field of Search ................................... 128/842, 844, 128/918, 885, DIG. 25; 604/347–353

[56] References Cited

U.S. PATENT DOCUMENTS

| | | | |
|---|---|---|---|
| 3,203,420 | 8/1965 | Lockhart | 604/353 |
| 3,999,550 | 12/1976 | Martin | 604/353 |
| 4,588,397 | 5/1986 | Giacalone | 604/351 |
| 4,589,875 | 5/1986 | Stringer | 604/351 |
| 4,738,673 | 4/1988 | Shepard | 604/349 |
| 5,330,455 | 7/1994 | McKay | 604/345 |

*Primary Examiner*—Michael A. Brown
*Attorney, Agent, or Firm*—Stuart E. Krieger

[57] ABSTRACT

A male incontinence device has one coupling part 200 attachable to a silicone pad 500 and a second coupling part 300 attached to a condom-like drainage member 400. A stretchable ring or wall 312 can be shifted ("snapped") by manual pressure between a locking position wherein the two coupling parts are locked together and an unlocking position wherein the two coupling parts can be separated to permit removal of the condom-like drainage member from the silicone pad.

6 Claims, 4 Drawing Sheets

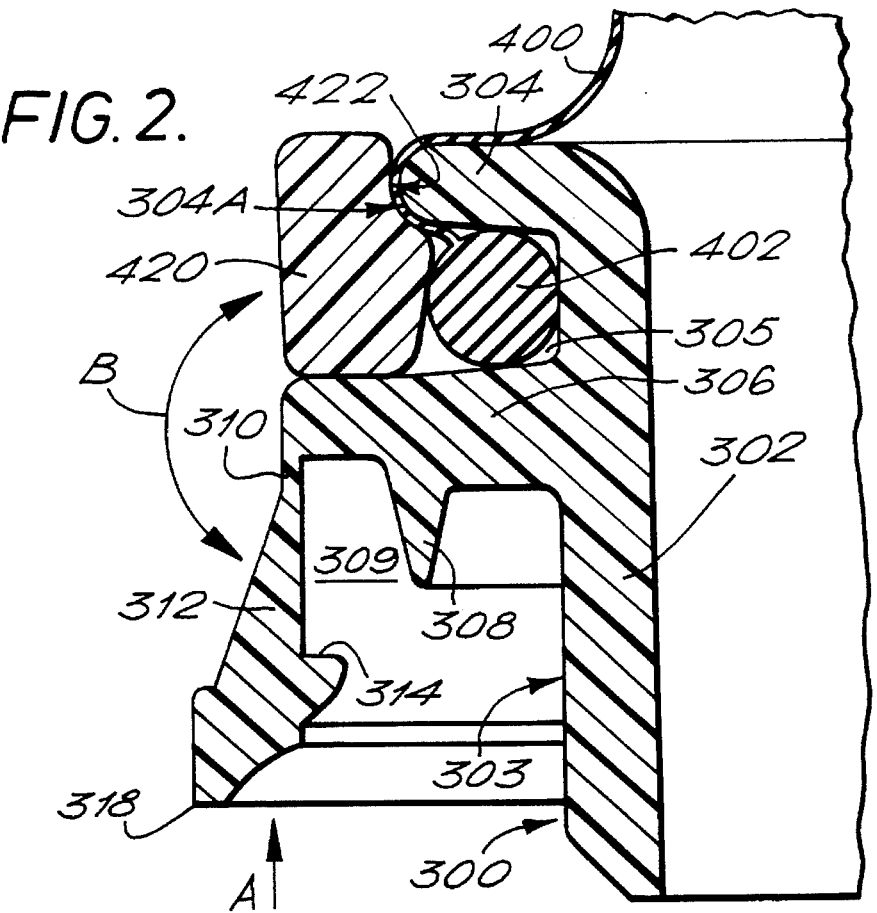
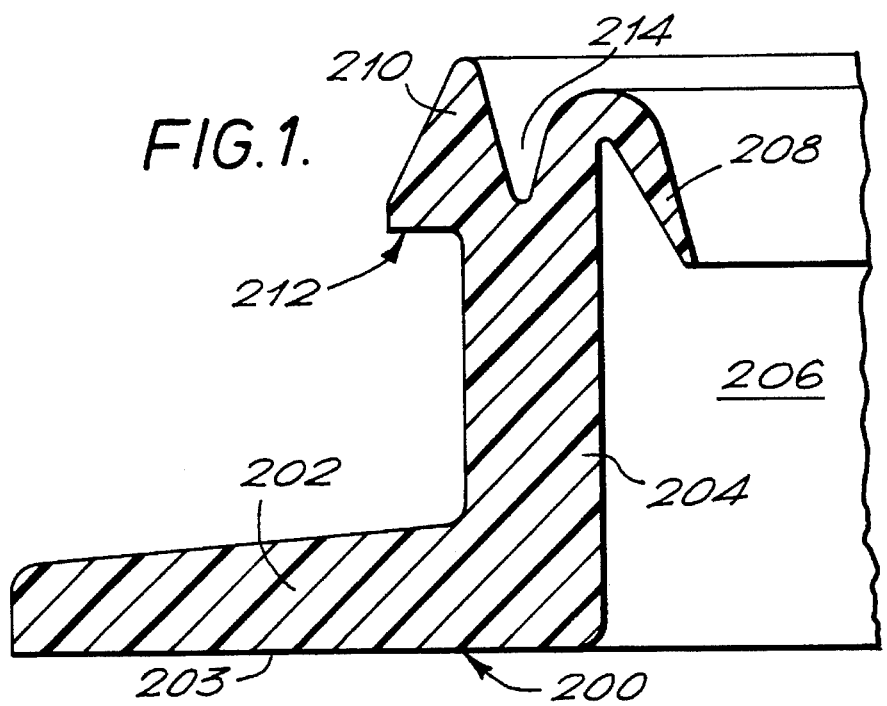

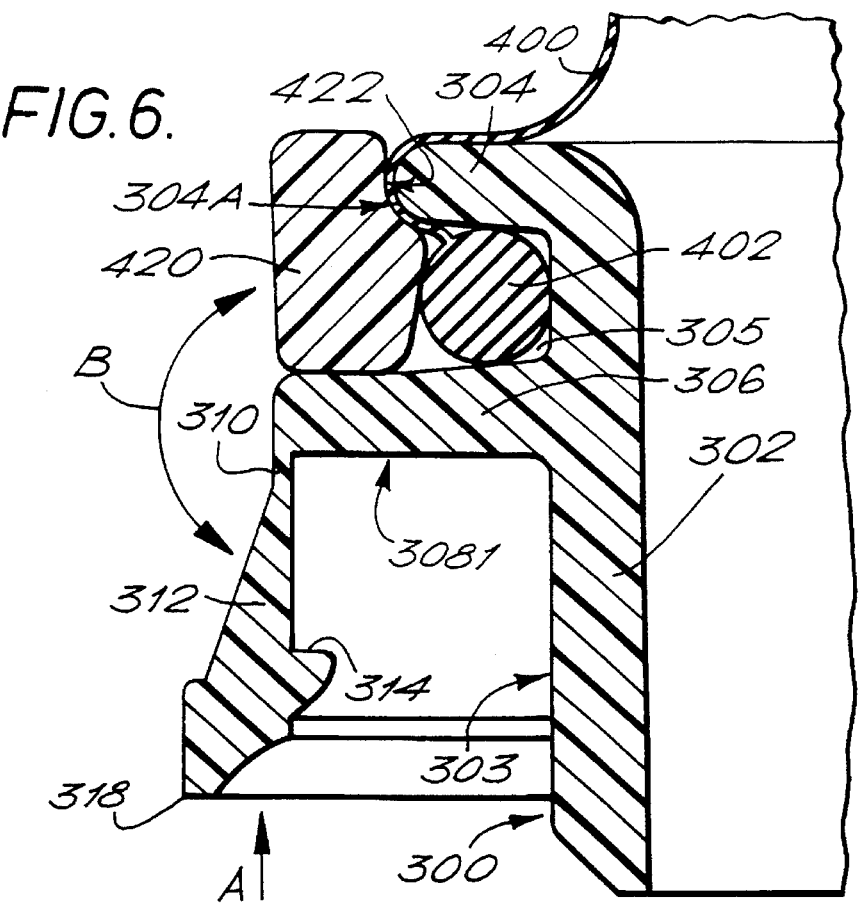
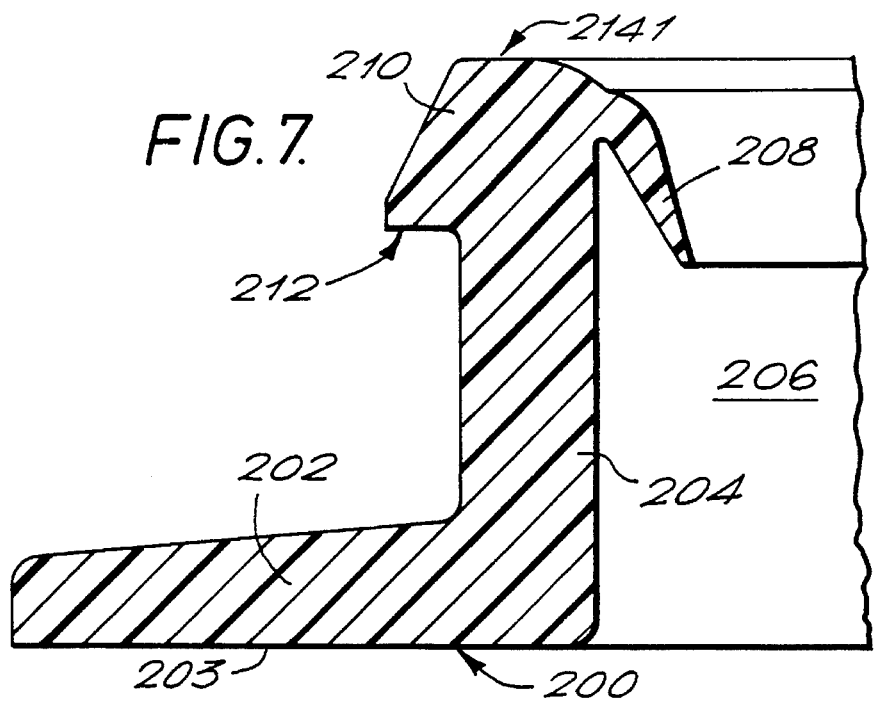

MALE INCONTINENCE DEVICE

This invention relates to a male incontinence device. Examples of known male incontinence devices can be seen in British Patents Nos. 669063, 1304544, 1459486, and 1521064. An early design of one of the present inventors is seen in British Patent No. 2048680.

The main retirements for a satisfactory male incontinence device are that it should be constructed to avoid leakage, be comfortable to wear, and be easy to manipulate and to put on and take off.

According to one aspect of the present invention, there is provided a male incontinence device which comprises first and second generally annular coupling parts, one being for attachment to the body of the wearer and having a substantially flat flange for this purpose with a penile orifice generally centrally located therein, the flange being connected to or integral with a orifice-surrounding sleeve, and the second part having a tubular member which extends at least part-way into the sleeve, the two parts having inter-engaging coupling structures and there being a rim which extends radially outwardly from the tubular member, the rim being integral with a flip-over bi-stable annulus connected by a plastics hinge to the radially outer portion of the rim, whereby the annulus in one of its positions serves to lock the two parts together and in the other of its positions permits them to be separated.

It is seen that there is provided a male incontinence device in which a strechable ring or periphery of one coupling element can be shifted ("snapped") by manual presssure between two positions, namely a locking position wherein the two coupling elements are locked together and an unlocking position wherein the two coupling elements can be separated to permit disassembly of the male incontinence device.

According to another aspect of the present invention, there is provided a male incontinence device which includes first and second coupling parts, the first coupling part comprising a flange from which extends an approximately cylindrical rib, the rib having a flexible and deflectable seal strip located radially inwardly thereof, and a second coupling part which has a base wall attached to an approximately annular wall positioned for engagement with, and so as to be encircled by, the seal strip on the first coupling part, the second coupling part also having an outer wall of resilient stretchable or deflectable synthetic plastics material which is joined to the base wall by an integral plastics hinge and which can be snapped between two limiting positions by finger action, the wall in its first or "open" position extending generally outwardly of the base wall and in its second or "closed" position making a locking engagement with a radially outer portion of the first coupling element; the first coupling part being connected to or integral with a soft and resilient pad which is shaped to apply, when worn, a pressure to an annular skin area of the wearer, surrounding the base of the penis.

With this design a positive, effective and reliable locking together of the two coupling parts is achieved, and the device is comfortable to wear and easy to uncouple.

With an arrangement as described above, by finger leverage, the outer wall of the second coupling part can be "snapped" between respective closed and open positions. In its open position, the two coupling parts can readily be separated. For this purpose, if desired, one or more gripping tabs can be placed on the second part. It is preferably located at the "12 o'clock" position on the exterior of the outer wall of the second coupling part. In the closed position of the outer wall, the preferred construction is such that there is a detent or locking relationship existing between an overhang on the radially outer rim of the cylindrical rib and a step on the radially inner surface of the outer wall of the second coupling part.

The invention will be better understood from the following illustrative and non-limiting particular description of embodiments thereof, given with reference to the accompanying illustrative drawings, in which like parts are denoted by like reference numerals and in which:

FIG. 1 is a diametral cross-sectional view of a first coupling part of a male incontinence device according to a preferred embodiment of the invention, showing only one end of the diameter, the other end being similar but of course a mirror-image;

FIG. 2 is a similar view of a second coupling part of a male incontinence device designed to co-operate with the first part shown in FIG. 1, the section being taken on the line I—I in FIG. 3;

FIG. 6 is a view similar to FIG. 1, but showing a second embodiment of the invention; and FIG. 7 is a view similar to FIG. 2, of the second embodiment.

Referring to FIGS. 1 and 2, the first coupling part 200 of the male incontinence device shown therein is circular in form and comprises a flange 202 and an approximately cylindrical rib or sleeve 204. While in the present particular description of the invention, reference is made to a cylindrical rib and approximately circular coupling parts, it will be appreciated that a satisfactory male incontinence device could be made whose coupling parts are not circular or cylindrical. For example, an incontinence appliance could be made with a central orifice which is rectangular or square with rounded corners, or with an orifice of other shape. The disclosure and claims in this patent application are accordingly not to be regarded as limited to geometrically circular constructions of male incontinence couplings.

Figure 4:
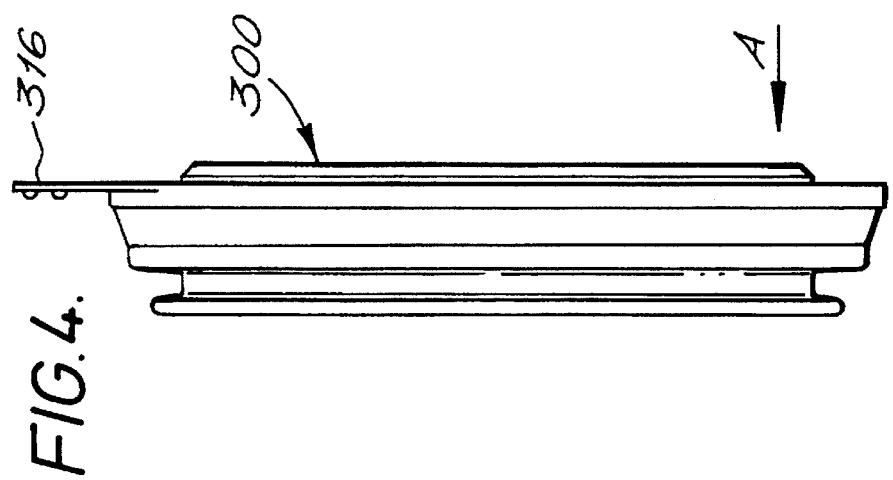
FIG. 4 is a side view of the part shown in FIG. 3.
Figure 5:
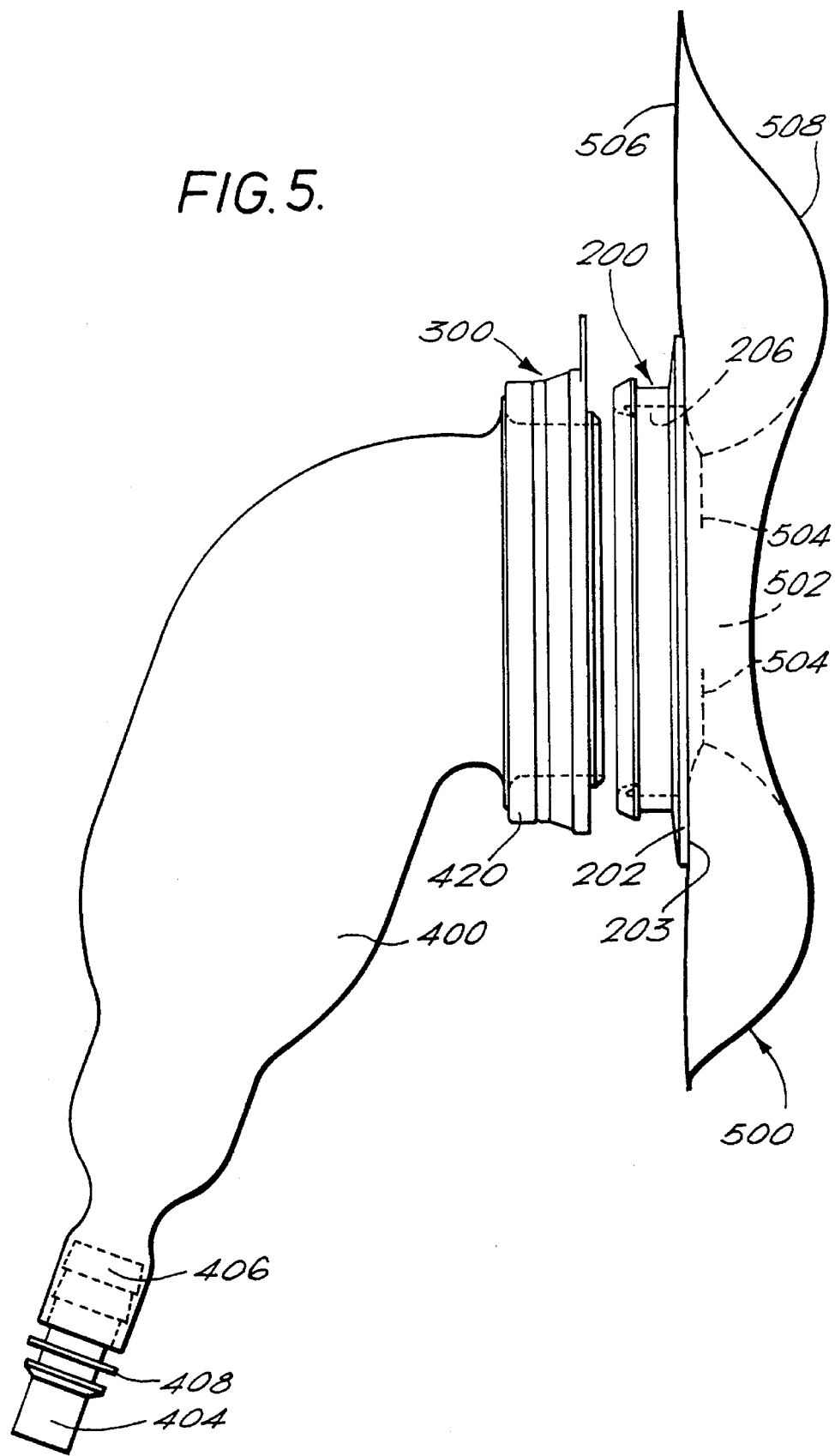
FIG. 5 is a side view, on a reduced scale compared to FIG. 2, showing one the two coupling parts slightly separated, with one coupling part connected to a soft and resilient pad which is held against the body of the wearer; the penis being seen inserted through a generally central hole in the pad.

FIGS. 1–5 show a male incontinence device which has two coupling parts, the first part 200 and a second part 300. These two parts are designed to be coupled together so as to provide a male incontinence device worn on the body, and which carries a conventional condom-like sheath, the free or lower end of the condom having an outlet pipe or spigot (see FIG.5). The first male incontinence part 200 comprises a substantially flat annular flange 202 made in one piece with a generally tubular sleeve 204. As seen in FIG. 5, the surface 203 of the flange 202 is attached to a flexible, soft, resilient pad 500 which may for example be made of a silicone elastomer. As particularly described and illustrated herein, the coupling parts of the male incontinence device are bodies of revolution but it will be appreciated that equivalent results could be obtained with a male incontinence device of, for example, generally oval form. Consequently, in the present disclosure, references to "circular", "cylindrical", and "annular" are to be interpreted as comprehending devices of closed loop shape. However, the preferred version of the invention is, as stated, a body of revolution.

The first part 200 (see particularly FIG. 1) comprising flange 202 and sleeve 204 encircles a penile orifice 206. Mounted on the radially interior surface of the sleeve 204 is a flexible and deflectible seal 208. This is of plastics material and is preferably integral with the sleeve 204 and the flange 202. At the upper end as seen in FIG. 1 of the part 200, there is provided a rib 210 which is located radially outwardly of, and adjacent to, a groove 214. The rib 210 has an undersurface 212 whose function will become apparent later in this description. The first part 200 described is preferably manufactured as a single moulding, and may be moulded from polyureythane. Suitable polyureythane is supplied by B. F. Goodrich, of Hounslow, Middlesex TW3 4EB.

The second part of the male incontinence device, part 300, (FIG. 2) comprises a tubular member 302 which is generally cylindrical in form, and the lower end of which, as seen in FIG. 2, comprises a spigot which is insertable into the orifice 206 illustrated in FIG. 1. The tubular member 302 is flared at its outer (upper as seen in FIG. 2) end to provide a retention flange 304 defining an annular recess 305. The rolled up end of a stretchable latex or equivalent condom 400 is stretched over the flared end 304 as seen in FIG. 5 and contracts to occupy the annular recess 305 and to grip onto the outer wall of the tubular member 302 as seen in FIG. 2. In this way, any conventional condom can be securely retained on the second part 300. In FIG. 2, the bead at the open end of the condom 400 is seen at 402. A spigot 404 (FIG.5) is inserted in a narrowed lower portion 406 of the condom 400. The spigot has a fitting or connecting rim 408 which enables it to be connected to a fitting for a tube or sleeve such as the fitting shown at FIG. 2 of U.K. Patent No. 2092690. A ring 420, of resilient, slightly stretchable synthetic plastics material, is provided to hold the bead 402 and an adjacent short length of the condom in position over the outwardly-extending flange 304. For this purpose, the preferred configuration of ring 420 has an interior surface which is curved to provide a smoothly-curved recess 422 shaped to be complementary to the curved outer surface 304A of the annular flange 304. In this way, an adequate security of attachment between the condom 400 and the coupling part 300 is achieved, while still permitting an easy assembly and disassembly of the incontinence device.

Part-way along the length of the tubular sleeve 302, a radially-extending rim 306 is located. This rim 306 carries an annular rib 308 and the free (diametrally outer) edge of the rim 306 is made in one piece with an integral plastics hinge 310, which connects the rib 306 to a flip-over annulus 310. The parts 300–312 mentioned are made in one piece as a single plastics moulding. One suitable material for such a moulding is EVA UL-00206 available from Esso Chemicals, but other suitable synthetic plastics materials may be employed. The flip-over annulus 312 is of an approximately triangular shape as seen in cross-section in FIG. 2 and has a radially inwardly-extending ledge 314. This ledge 314 is, however, radially inwardly-extending in the position of the annulus 312 illustrated in FIG. 2. In its alternative stable position, to which it can be flipped by moving it as shown by the arrow B, the ledge 314 is radially outwardly-extending. The purpose of the ledge 314 is to engage under the surface 212 shown in FIG. 1, and this engagement gives a secure and reliable locking together of the first part 200 and the second part 300. To move the flip-over flange 312 from its first or locking position to its second or unlocking position (the locking position being illustrated in FIG. 2) can readily be done by finger manipulation.

Figure 3:
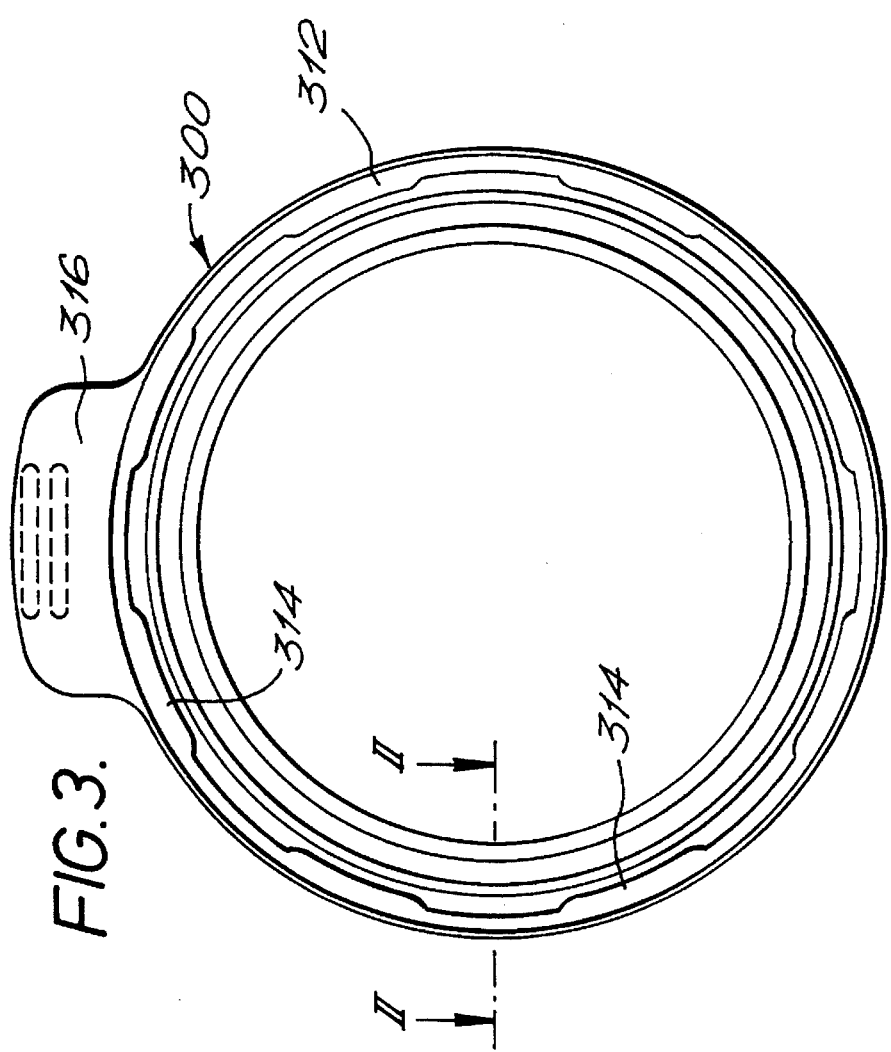
FIG. 3 is a front view on a reduced scale, looking in the direction of the arrow A in FIGS. 2 and 4 of the second part, seen with the flip-over annulus in its locking position.

Referring now to FIGS. 3 and 4, these show the second part 300 and illustrate a grasping tab 316 which is located on the radially outer edge 318 of the outer wall 312. This tab is provided to enable a wearer to grasp it and start to separate the two parts 200, 300, while still holding the flange 202 of the first part 200 safely on the wall of the abdomen.

FIG. 4 illustrates in side view the second part of the male incontinence device illustrated in FIGS. 1–5.

Referring now to FIG. 5, a silicone elastomer pad 500 is attached in any convenient way to the surface 203 of the first part 200. The pad 500 has a central hole 502 in substantial registry with the central hole 206 of the part 200, and an inwardly-extending thin annular flap 504 of plastics film, has radially-extending cuts or slots to provide a degree of tolerance so that the device will fit comfortably on men of varying sizes. The surface 506 which attaches to the surface 203 is substantially flat, but the surface 508 intended to contact the wearer, is curved in 3 dimensions to provide a composite shape which is comfortable on the body when the penis is inserted through the aligned holes 502 and 206. The pad 500 consequently makes a secure and comfortable engagement with the body of the wearer and is held on by straps, or by a belt, or by being worn within elasticated briefs.

When the parts 200 and 300 are coupled together, the rib 308 extends into the groove 214, and the rib 210 extends into the recess 309 disposed between the rib 308 and the flip-over annulus 312. The flexible deflectible seal strip 208 makes close sealing contact with the cylindrical surface 303 of the tubular member 302. Due to this close, secure and snug interengagement between the parts 200 and 300, the likelihood of liquid escape or leakage is substantially avoided or at least greatly reduced.

It will be seen that according to this embodiment of the invention, there has been provided a simple to manipulate, substantially leak-proof, robust, effective and comfortable male incontinence device.

A second embodiment of the invention is shown in FIGS. 6 and 7. This embodiment is similar to the first embodiment except that the annular rib 308 and the resulting recess shown in FIG. 1 and the groove 214 shown in FIG. 2 are not included. Instead, the sleeve 204 has an annular flat end surface 2141 which, when the coupling parts are coupled, engages the annular surface 3081 of the radiallly extending rim 306. The operation of the coupling parts shown in FIGS. 6 and 7 is essentially the same as that of the coupling parts 200 and 300 of FIGS. 1 and 2.

Those skilled in the art of design of male incontinence devices will realise that certain changes and modifications may be made, without departing from the present invention.

We claim:

1. A male incontinence device comprising:

a first coupling assembly having a first penile orifice, said first coupling assembly having a rib projecting therefrom with an engageable undersurface;

a second coupling assembly having a second penile orifice, said second coupling assembly having a peripheral rim, said rim including a flip-over bi-stable annulus member extending therefrom, said annulus member being stable in a flipped-down closed position and a flipped-up open position; said rim having a preformed and predeterminedly dimensioned recess for receiving said rib when said annulus is in said flipped-up open position for aligning said first and second coupling assemblies for coupling when said rib is received in said recess, and for mating with and capturing said rib when said annulus is in said flipped-down closed position, said rim also including a predefined and preformed hinge about which said bi-stable annulus is pivotable into said open and closed positions; said annulus member having a catch, said catch capable of engaging said rib undersurface when in a flipped-down closed position so as to couple together said first and second coupling assemblies, said first and second penile orifices being fixedly aligned when said first and second coupling assemblies are coupled together, said coupled assemblies being separable when said annulus member is in a flipped-up open position; and means for securing a male condom catheter to one of said coupling assemblies.

2. The male incontinence device of claim 1 further comprising an open-ended male condom catheter securable to one of said coupling assemblies with an open end aligned with said penile orifice.

3. The male incontinence device of claim 2 wherein said condom catheter has a bead, said means for securing includes an annular ring and cooperating groove, said bead being securable between said annular ring and groove.

4. The male incontinence device of claim 1 wherein said second coupling assembly is integral and is composed of plastic material.

5. The male incontinence device of claim 1 wherein one of said coupling assemblies is attached to a soft and resilient pad adapted to be placed against the skin of the wearer so as to surround the penis.

6. The male incontinence device of claim 1 wherein one of said coupling assemblies has a cylindrical projection and said other assembly has a cylindrical recess for receiving said cylindrical projection, said first and second coupling assemblies being aligned for coupling together when said cylindrical projection is received in said cylindrical recess.

* * * * *